United States Patent
Fink et al.

(10) Patent No.: US 10,565,350 B2
(45) Date of Patent: *Feb. 18, 2020

(54) IMAGE PROCESSING AND TEXT ANALYSIS TO DETERMINE MEDICAL CONDITION

(71) Applicant: International Business Machines Corporation, Armonk, NY (US)

(72) Inventors: Patrick W. Fink, Charlotte, NC (US); Kristin E. McNeil, Charlotte, NC (US); Philip E. Parker, York, SC (US); David B. Werts, Charlotte, NC (US)

(73) Assignee: International Business Machines Corporation, Armonk, NY (US)

( * ) Notice: Subject to any disclaimer, the term of this patent is extended or adjusted under 35 U.S.C. 154(b) by 92 days.

This patent is subject to a terminal disclaimer.

(21) Appl. No.: 15/639,341

(22) Filed: Jun. 30, 2017

(65) Prior Publication Data

US 2017/0300624 A1   Oct. 19, 2017

Related U.S. Application Data

(63) Continuation of application No. 15/067,663, filed on Mar. 11, 2016.

(51) Int. Cl.
*G06F 19/00*    (2018.01)
*G16H 50/20*    (2018.01)
*G06F 16/583*   (2019.01)

(52) U.S. Cl.
CPC ........ *G06F 19/321* (2013.01); *G06F 16/5838* (2019.01); *G16H 50/20* (2018.01)

(58) Field of Classification Search
None
See application file for complete search history.

(56) References Cited

U.S. PATENT DOCUMENTS 6,052,481 A      4/2000  Grajski et al.
6,760,714 B1 *   7/2004  Caid ................. G06K 9/4623
                                                         706/14

(Continued)

FOREIGN PATENT DOCUMENTS

WO     2008114016     9/2008

OTHER PUBLICATIONS

Friedman et al., "Natural Language and Text Processing in Biomedicine", http://www.download.springer.com//, 2006.

(Continued)

*Primary Examiner* — Mark Roz
(74) *Attorney, Agent, or Firm* — Joseph Polimeni; Edell, Shapiro & Finnan, LLC

(57) ABSTRACT

A method, a processing device, and a computer program product are provided. At least one processing device correlates textual medical information related to the subject with characteristics of an image of a medical condition of the subject to generate a subject signature. The at least one processing device compares the subject signature with multiple reference signatures to determine at least one reference signature corresponding to the subject signature. Each reference signature is associated with a corresponding medical condition and is generated by correlating textual medical information regarding the corresponding medical condition with characteristics of an image of the corresponding medical condition. The at least one processing device identifies the medical condition of the subject based on the medical conditions associated with the determined at least one reference signature. Information is provided regarding the identified medical condition of the subject.

20 Claims, 3 Drawing Sheets

(56) References Cited

U.S. PATENT DOCUMENTS

| | | |
|---|---|---|
| 7,234,106 B2 | 6/2007 | Simske |
| 7,260,249 B2 | 8/2007 | Smith |
| 8,321,383 B2 | 11/2012 | Schumacher et al. |
| 8,538,770 B2 | 9/2013 | Papier et al. |
| 8,751,259 B2 | 6/2014 | Wang |
| 8,953,858 B2 | 2/2015 | Becker et al. |
| 10,198,816 B2 | 2/2019 | Steigauf et al. |
| 10,318,092 B2 | 6/2019 | Aleksovski |
| 2003/0105638 A1 | 6/2003 | Taira |
| 2004/0267740 A1* | 12/2004 | Liu .................. G06F 16/58 |
| 2006/0136259 A1 | 6/2006 | Weiner et al. |
| 2007/0160275 A1* | 7/2007 | Sathyanarayana .... G06F 19/321 |
| | | 382/128 |
| 2010/0114597 A1 | 5/2010 | Shreiber et al. |
| 2011/0026789 A1 | 2/2011 | Hsu et al. |
| 2011/0249905 A1 | 10/2011 | Singh et al. |
| 2013/0040274 A1 | 2/2013 | Rath et al. |
| 2013/0311502 A1 | 11/2013 | Takata et al. |
| 2014/0016846 A1 | 1/2014 | Blaskovics et al. |
| 2014/0257854 A1 | 9/2014 | Becker et al. |
| 2018/0032676 A1 | 2/2018 | Mabotuwana et al. |
| 2018/0137941 A1 | 5/2018 | Chen |

OTHER PUBLICATIONS

List of IBM Patents or Patent Applications Treated as Related, Jul. 2017, 1 page.

Final Office Action in U.S. Appl. No. 15/067,663, dated Jul. 22, 2019, 22 pages.

Non-Final Office Action in U.S. Appl. No. 15/067,663, dated Feb. 21, 2019, 16 pages.

* cited by examiner

IMAGE PROCESSING AND TEXT ANALYSIS TO DETERMINE MEDICAL CONDITION

CROSS-REFERENCE TO RELATED APPLICATIONS

This application is a continuation of U.S. patent application Ser. No. 15/067,663, entitled "IMAGE PROCESSING AND TEXT ANALYSIS TO DETERMINE MEDICAL CONDITION" and filed Mar. 11, 2016, the disclosure of which is incorporated herein by reference in its entirety.

BACKGROUND

Present invention embodiments are related to systems and methods for image processing and textual analysis. In particular, present invention embodiments are related to performing textual analysis on unstructured text describing symptoms of a patient's medical condition, correlating textual data and characteristics generated from processing of an image of the patient's medical condition to produce a subject signature, and finding a closest match to a reference signature related to a textual description of a known medical condition and an image of the known medical condition.

Most medical conditions are best treated if identified early. However, it is difficult for an average person to know about various medical conditions and related symptoms. Often, one may have a serious medical condition and not know it or one may assume it is a different medical condition. It is inconvenient, time-consuming and costly to go to a doctor's office for every suspected medical condition, large or small.

SUMMARY

According to embodiments of the present invention, a computer-implemented method, a processing device, and a computer program product are provided. Embodiments may be implemented by at least one processing device. Textual medical information related to a subject may be correlated with characteristics of an image of a medical condition of the subject to generate a subject signature. The subject signature may be compared with multiple reference signatures to determine at least one reference signature corresponding to the subject signature. Each reference signature is associated with a corresponding medical condition and is generated by correlating textual medical information regarding the corresponding medical condition with characteristics of an image of the corresponding medical condition. The medical condition of the subject may be identified based on the medical conditions associated with the determined at least one reference signature. Information regarding the identified medical condition of the subject may be provided.

BRIEF DESCRIPTION OF THE DRAWINGS

Generally, like reference numerals in the various figures are utilized to designate like components.

DETAILED DESCRIPTION

Figure 1:
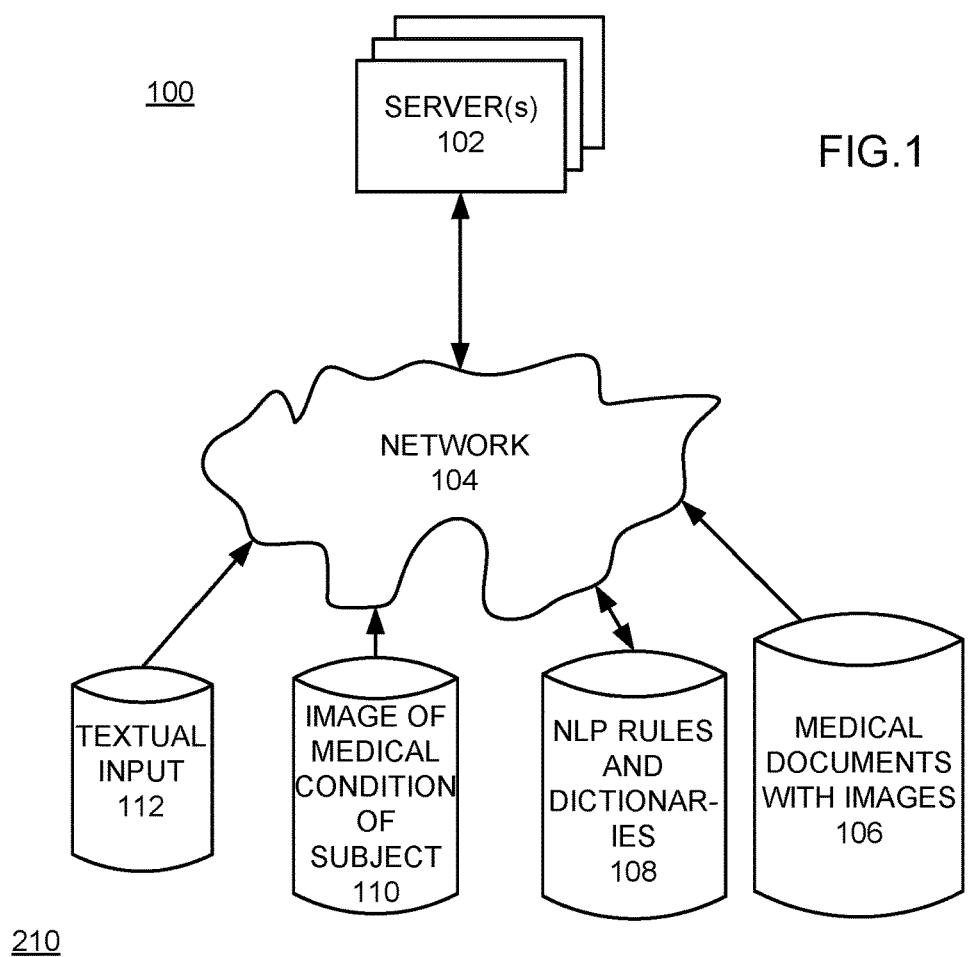
FIG. 1 illustrates an example environment in which embodiments may be implemented.

With reference now to FIG. 1, an example environment 100 for implementation of embodiments is shown. Example environment 100 may include one or more servers 102, a network 104, and one or more databases, which may include unstructured textual input 112, an image of a medical condition of a subject 110, natural language processing (NLP) rules and dictionaries 108 and medical documents including images of known medical conditions 106. Although FIG. 1 shows four databases, each of which may include unstructured textual input 112, an image of a medical condition of a subject 110, natural language processing (NLP) rules and dictionaries 108 and medical documents including images of known medical conditions 106, other embodiments may include this data in a single database or this data may be included in a different number of databases.

Network 104 may be implemented by any number of any suitable communications media (e.g., wide area network (WAN), local area network (LAN), Internet, Intranet, etc.). In some embodiments, server(s) 102 and NLP rules and dictionaries 108 may be local to each other and may communicate with each other via any appropriate local communication medium (e.g., local area network (LAN), hardwire, wireless link, Intranet, etc.). In other embodiments, server(s) 102 and NPL rules and dictionaries 108 may be remotely located from each other and may communicate with each other via a WAN, Internet, etc.

In a training phase, one or more server(s) 102 may receive copies of medical documents 106, which may include images of known medical conditions as well as doctors' notes, medical journal entries, and academic medical articles related to the known medical conditions. Server(s) 102 may use NLP rules and dictionaries 108 to extract known medical condition descriptions from unstructured text included in medical documents 106. Images of the corresponding known medical conditions may be analyzed to extract image characteristics. For each of the known medical conditions, a corresponding extracted known medical condition description may be correlated with respective extracted image characteristics to produce a reference signature for each of the known medical conditions.

In a runtime phase, one or more processing devices 102 may receive unstructured textual input 112 including a description of a subject's medical condition and may use NLP rules and dictionaries 108 to extract a subject's medical condition description from unstructured textual input 112. A subject may be a person, animal, or other entity having a medical or other condition. An image of the subject's medical condition may be analyzed to extract image characteristics. The subject's extracted medical condition description and the extracted image characteristics of the subject's medical condition may be correlated to produce a subject's medical condition signature. One or more reference signatures that are closest to the subject's medical condition signature may be selected and results displayed to a user. The embodiments may alternatively be utilized for any type of entity (persons, animals, objects, etc.) having any desired visual characteristics to determine a condition of the entity.

Figure 2:
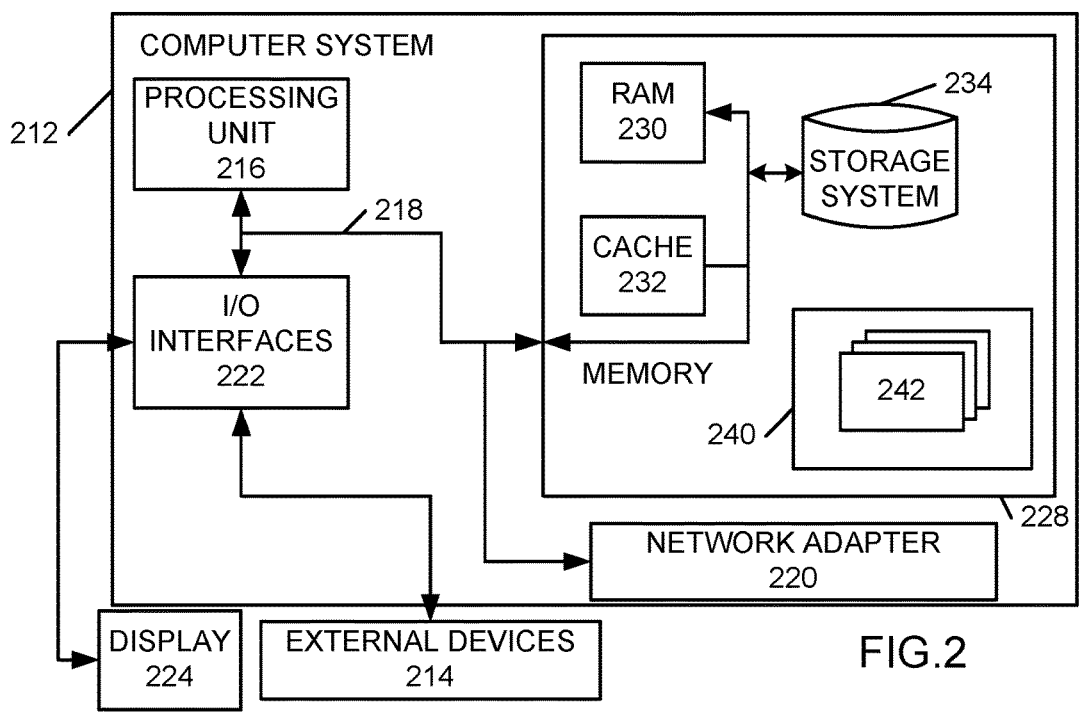
FIG. 2 illustrates an example of a processing device capable of performing functions of various embodiments.

Referring now to FIG. 2, a schematic of an example processing device 210 is shown, which may implement a server of server(s) 102. Processing device 210 is only one example of a suitable processing device for the environment of FIG. 1 and is not intended to suggest any limitation as to the scope of use or functionality of embodiments of the invention described herein. Regardless, processing device 210 is capable of being implemented and/or performing any of the functionality set forth herein.

In processing device 210, there is a computer system 212 which is operational with numerous other general purpose or special purpose computing system environments or configurations. Examples of well-known computing systems, environments, and/or configurations that may be suitable for use with computer system 212 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules, being executed by a computer system. Generally, program modules may include routines, programs, objects, components, logic, data structures, and so on that perform particular tasks or implement particular abstract data types. Computer system 212 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 2, computer system 212 is shown in the form of a general-purpose computing device. Components of computer system 212 may include, but are not limited to, one or more processors or processing units 216, a system memory 228, and a bus 218 that couples various system components including system memory 228 to one or more processors 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and includes both volatile and non-volatile media, and removable and non-removable media.

System memory 228 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and program data or some combination thereof, may include an implementation of a networking environment. Program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 220. As depicted, network adapter 220 communicates with the other components of computer system 212 via bus 218. It should be understood that, although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 3:
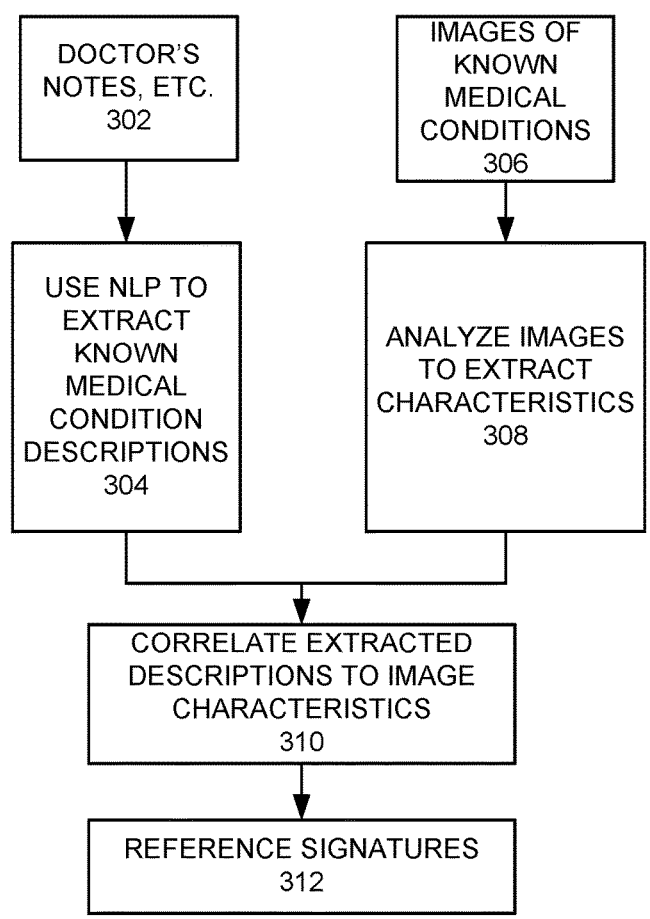
FIG. 3 is a flowchart illustrating example processing regarding generation of reference signatures.

FIG. 3 is a flowchart that illustrates example processing in a training phase of an embodiment. The process may begin with one or more processing devices 102 inputting medical documents 106, which may include unstructured textual input as well as images of known medical conditions (act 302). The unstructured textual input may include, but not be limited to, doctors' notes, medical journal articles and academic medical articles related to known medical conditions or other unstructured text having a description of the subject's medical condition. One or more processing devices 102 may use NLP rules and dictionaries 108 to extract known medical condition descriptions from the unstructured textual input included in medical documents 106 (act 304).

One industry standard for context analytics is Unstructured Information Management Architecture (UIMA). UIMA is an architecture that includes software systems for analyzing large volumes of unstructured information in order to discover knowledge that is relevant to an end user. For example, a UIMA application may process text and identify entities, such as persons, places, organizations, or relations such as works-for or located-at. A UIMA pipeline is a list of individual stages, or Annotators, which are run serially. When a document is processed by the UIMA pipeline, a first annotator stage may create annotations covering sections of text. When the first stage is completed, the second annotator stage may then process the text. Each subsequent stage may read annotations created by earlier stages and may add or modify the annotations, thus building up a more complex analysis of contents of the document. The annotations could be for an entire document, a paragraph or sentence, a token or an annotation that one can define by creating a custom dictionary or a parsing rule including, but not limited to, a city, a disease, or a date of birth.

Another product for context analysis is IBM Advanced Care Insights from International Business Machines of Armonk, N.Y. IBM Advanced Care Insights has dictionaries for identifying various medical conditions and symptoms. Further, one may define custom dictionaries and rules for use with various embodiments. Some examples of custom dictionaries may include a date dictionary having words including, but not limited to, today, yesterday, January, February, March, etc. An example symptom dictionary may have words including, but not limited to, headache, pain, anxiety, bleeding, and swollen. An example rule may be as follows, where a token is a span of text:

<Date> <tokens> <Symptom>
<Symptom> <tokens> <Date>

Returning to the flowchart of FIG. 3, server(s) 102 may input images of known medical conditions from medical documents 106 (act 306). Conventional image analysis techniques may be used to extract image characteristics of the input images (act 308). Some conventional image analysis techniques, which may be used in various embodiments, include, but are not limited to, detecting boundaries within an image and facial recognition.

Conventional machine learning techniques may be employed in a correlation module engine in order to correlate each extracted known medical condition description with image characteristics of a corresponding image of the known medical condition (act 310) to produce reference signatures (act 312).

An example signature could be a description of a cancerous mole on the skin collocated with an image of the ailment. "Irregular shaped", "darkened skin", "surrounded by slightly reddish irritation area" could all appear in the text surrounding the image, along with text unrelated to the image. Key components could be represented as a vector such as [0 0 1 0 0 1 1 0 0], where the is may be positional markers for image features that can be detected and are described in a given sentence. The 0s may be features that can be looked for in all images, but are not present in a textual description. An example of things in the image that do not appear in the textual description may include, but not be limited to, many small discolorations, raised skin, linear marks (scars), linear tears (cuts), etc.

Using conventional techniques, image analytics can identify shapes and colors, and can identify patterns such as, for example, facial recognition when seeing 2 circles for eyes, a line for a nose, and so on. A deviation from a pure circle/oval can be captured if it exceeds a threshold as an "irregular shaped" feature. Darkened skin can be captured via color filters as another feature. A combination of a color filter and a shape detector could capture a reddish ring as another feature. Again, the image analytics would produce a feature vector representing the things found in the image.

The feature vector produced by the image analytics may be correlated with the feature vector produced by NLP to arrive at a disease causing the anomalies to appear. For example, if the sentence was "Skin cancer symptoms can include irregular shaped darkened skin surrounded by slightly reddish irritation area", the signature could be associated with "skin cancer". Additional symptoms described in the text could be stored along with symptoms of the main disease for later display to a user regarding things not apparent in the image.

Figure 4:
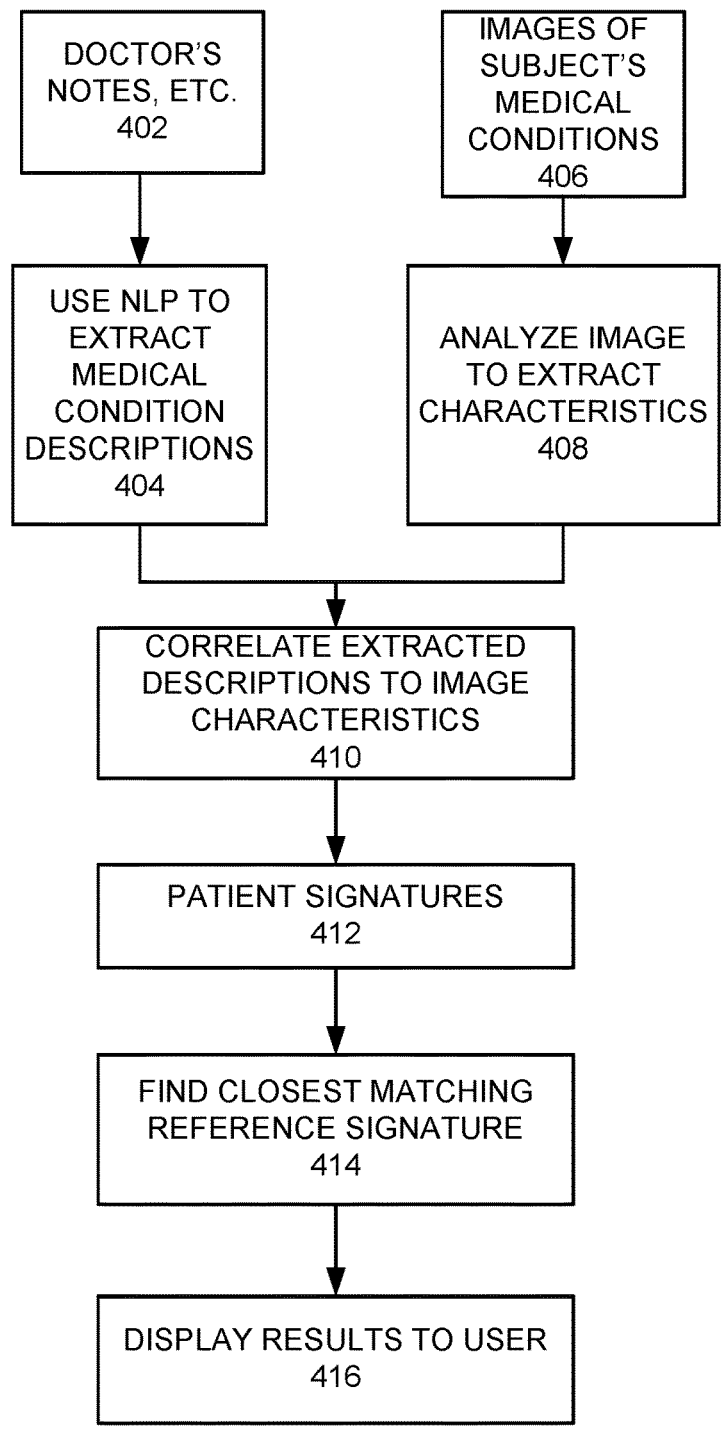
FIG. 4 is a flowchart illustrating example processing regarding generating a subject signature and finding a closest match to one or more reference signatures.

FIG. 4 is a flowchart that illustrates example processing in a runtime phase of an embodiment. The process may begin with server(s) 102 inputting textual input 112 (act 402). Textual input 112 may include unstructured textual input including, but not limited to, doctors' notes, subject's notes, social media messages, email and text messages. Server(s) 102 may use NLP rules and dictionaries 108 to extract medical condition descriptions from textual input 112 (act 404). Conventional analytics including, but not limited to, UIMA and IBM Advanced Care Insights may be used to annotate textual input 112 and extract medical condition descriptions in substantially the same manner as described above.

An image of a subject's medical condition may be received (act 406) and may be analyzed, using conventional image analysis techniques, to extract image characteristics (act 408). Server(s) 102 may correlate the extracted medical condition descriptions with the image characteristics (act 410) to produce a patient or subject signature (act 412). The subject signature may be compared with each of a number of reference signatures to determine one or more closest matching reference signatures (act 414). A match score may be computed. The one or more closest matching reference signatures may be determined by the match score, which may be based on computing a distance of a feature vector of the subject signature from a corresponding feature vector of each of the reference signatures. The one or more closest matching reference signatures have a minimum distance with respect to the subject signature.

Distance computation is typically defined as a Euclidean distance between the vectors. In Euclidean space $\mathbb{R}^n$, this is defined as the square root of the sums of the squared differences of each position, i.e. $\sqrt{\Sigma_{i=1}^{n}|v_1(x_i)-v_2(x_i)|^2}$. Other possibilities may include magnitude difference or Hamming distance (simple count of how many bits are different in total).

Results, which may include information regarding the one or more closest matching reference signatures, may then be displayed to a user (act 416).

In one embodiment, a user, or doctor to prevent undue hypochondria, may use a user interface to take an image of something he or she is curious about, and may be presented with a descending list of matches about what the image shows. In another embodiment, a system may scan social media, and if a certain threshold of confidence is achieved, a message (social media message, email, text if known, etc.) may be sent to the person in the image to inform them of a likely medical condition.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and may communicate via any suitable communications medium (e.g., LAN, WAN, Intranet, Internet, hardwired, modem connection, wireless, etc.). For example, the functions of the present invention embodiments may be distributed in any manner among the various systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

We claim as our invention:

1. A computer-implemented method of identifying a medical condition of a subject, the computer-implemented method comprising:
   correlating, by at least one processing device, one or more medical descriptions extracted from textual medical information related to the subject with characteristics of an image of a medical condition of the subject to generate a subject signature, the correlating further comprising:
      analyzing the image of the medical condition of the subject to produce a feature vector representing features found in the image,
      produce a vector based on the one or more medical descriptions, each element of the vector having a first value representing a respective detectable image feature that is included in the one or more medical descriptions, and each element of the vector having a second value representing a respective detectable image feature that is not included in the one or more medical descriptions, and
      generate the subject signature based on the vector and the feature vector;
   comparing, by the at least one processing device, the subject signature with a plurality of reference signatures to determine a closest matching reference signature to the subject signature, wherein each reference signature is based on a corresponding second vector produced based on one or more reference medical descriptions extracted from textual medical information associated with a corresponding medical condition and a second feature vector representing features found in an image of the corresponding medical condition;
   identifying, by the at least one processing device, the medical condition of the subject based on the corresponding medical condition associated with the determined closest matching reference signature; and
   providing information regarding the identified medical condition of the subject.

2. The computer-implemented method of claim 1, wherein the medical condition includes a disease.

3. The computer-implemented method of claim 1, further comprising:
generating the plurality of reference signatures, the generating the plurality of reference signatures further comprising:
performing analytics on each of a plurality of textual medical information corresponding to a plurality of medical conditions to extract respective one or more reference medical descriptions of each of the plurality of medical conditions;
analyzing images of the plurality of medical conditions to extract respective image characteristics of each of the plurality of medical conditions; and
correlating the extracted respective one or more reference medical descriptions of each of the plurality of medical conditions with the corresponding extracted image characteristics to generate each of the reference signatures.

4. The computer-implemented method of claim 1, wherein the correlating the one or more medical descriptions extracted from the textual medical information related to the subject with the characteristics of the image of the medical condition of the subject to generate the subject signature comprises:
analyzing the textual medical information related to the subject to extract the one or more medical descriptions of the medical condition of the subject.

5. The computer-implemented method of claim 1, wherein the comparing the subject signature with a plurality of reference signatures comprises:
calculating a match score between the subject signature and each of the plurality of reference signatures; and
determining a closest matching reference signature corresponding to the subject signature based on the match scores.

6. The computer-implemented method of claim 5, wherein:
the characteristics of the image of the medical condition of the subject and the characteristics of the image of the corresponding medical condition include respective feature vectors; and
the calculating a match score between the subject signature and each of the plurality of reference signatures further comprises:
comparing the feature vector of the image of the medical condition of the subject with a respective second feature vector of each of the images of the corresponding medical conditions.

7. The computer-implemented method of claim 5, wherein the match score for a reference signature is based on a distance between the reference signature and the subject signature.

8. A computer program product comprising:
a computer readable storage medium having computer readable program code embodied therewith for execution on a processing system, the computer readable program code being configured to be executed by the processing system to:
correlate one or more medical descriptions extracted from textual medical information of a subject with characteristics of an image of a medical condition of the subject to generate a subject signature, the correlating further comprising the processing system being configured to:
analyze the image of the medical condition of the subject to produce a feature vector representing features found in the image,
produce a vector based on the one or more medical descriptions, each element of the vector having a first value representing a respective detectable image feature that is included in the one or more medical descriptions, and each element of the vector having a second value representing a respective detectable image feature that is not included in the one or more medical descriptions, and
generate the subject signature based on the vector and the feature vector;
compare the subject signature with a plurality of reference signatures to determine a closest matching reference signature to the subject signature, wherein each reference signature is based on a corresponding second vector produced based on one or more reference medical descriptions extracted from textual medical information associated with a corresponding medical condition and a second feature vector representing features found in an image of the corresponding medical condition;
identify the medical condition of the subject based on the corresponding medical condition associated with the determined closest matching reference signature; and
provide information regarding the identified medical condition of the subject.

9. The computer program product of claim 8, wherein the medical condition includes a disease.

10. The computer program product of claim 8, wherein each of the reference signatures is generated by:
performing analytics on each of a plurality of textual medical information corresponding to a plurality of medical conditions to extract respective one or more reference medical descriptions of each of the plurality of medical conditions;
analyzing images of each of the plurality of medical conditions to extract respective image characteristics of each of the plurality of medical conditions; and
correlating the extracted respective one or more reference medical descriptions of each of the plurality of medical conditions with the corresponding respective image characteristics to generate each of the reference signatures.

11. The computer program product of claim 8, wherein the correlating the one or more medical descriptions extracted from the textual medical information of the subject with the characteristics of the image of the medical condition of the subject to generate the subject signature further comprises:
analyzing the textual medical information of the subject to extract the one or more medical descriptions of the medical condition of the subject.

12. The computer program product of claim 8, wherein the comparing the subject signature with a plurality of reference signatures comprises;
calculating a match score between the subject signature and each of the plurality of reference signatures; and
determining the closest matching reference signature corresponding to the subject signature based on the match scores.

13. The computer program product of claim 12, wherein:
the characteristics of the image of the medical condition of the subject and the characteristics of the image of the corresponding medical condition include respective feature vectors; and the calculating a match score between the subject signature and each of the plurality of reference signatures further comprises:
comparing the feature vector of the image of the medical condition of the subject with a respective second feature vector of each of the images of the corresponding medical conditions.

14. The computer program product of claim 12, wherein the match score for a reference signature is based on a distance between the reference signature and the subject signature.

15. A processing device comprising:
at least one processor;
a memory; and
a communication bus connecting the at least one processor with the memory, wherein the memory has stored therein instructions, which when executed by the at least one processor cause the processing device to perform a method comprising:
correlating one or more medical descriptions extracted from textual medical information related to a subject with characteristics of an image of a medical condition of the subject to generate a subject signature, the correlating further comprising:
analyzing the image of the medical condition of the subject to produce a feature vector representing features found in the image,
producing a vector based on the one or more medical descriptions, each element of the vector having a first value representing a respective detectable image feature that is included in the one or more medical descriptions, and each element of the vector having a second value representing a respective detectable image feature that is not included in the one or more medical descriptions, and
generating the subject signature based on the vector and the feature vector;
comparing the subject signature with a plurality of reference signatures to determine a closest matching reference signature to the subject signature, wherein each reference signature is based on a corresponding second vector produced based on one or more reference medical descriptions extracted from textual medical information associated with a corresponding medical condition and a second feature vector representing features found in an image of the corresponding medical condition;
identifying the medical condition of the subject based on the corresponding medical condition associated with the determined closest matching reference signature; and
providing information regarding the identified medical condition of the subject.

16. The processing device of claim 15, wherein the medical condition includes a disease.

17. The processing device of claim 15, further comprising:
generating the plurality of reference signatures, the generating the plurality of reference signatures further comprising:
performing analytics on a plurality of textual medical information corresponding to a plurality of medical conditions to extract respective one or more reference medical descriptions of each of the plurality of medical conditions;
analyzing images of the plurality of medical conditions to extract respective image characteristics of each of the plurality of medical conditions; and
correlating the extracted respective one or more reference medical descriptions of the plurality of medical conditions with the corresponding respective image characteristics to generate the reference signatures.

18. The processing device of claim 15, wherein the correlating to generate the subject signature comprises:
analyzing the textual medical information related to the subject to extract the one or more medical descriptions of the medical condition of the subject.

19. The processing device of claim 15, wherein the comparing the subject signature with a plurality of reference signatures comprises:
calculating a match score between the subject signature and each of the plurality of reference signatures; and
determining the closest matching reference signature corresponding to the subject signature based on the match scores.

20. The processing device of claim 19, wherein:
the characteristics of the image of the medical condition of the subject and the characteristics of the image of the corresponding medical condition include respective feature vectors; and
the calculating a match score between the subject signature and each of the plurality of reference signatures further comprises:
comparing the feature vector of the image of the medical condition of the subject with a respective second feature vector of each of the images of the corresponding medical conditions.

* * * * *